US009895328B2

(12) United States Patent
Appling et al.

(10) Patent No.: US 9,895,328 B2
(45) Date of Patent: Feb. 20, 2018

(54) CALCIUM FORMATE AS A SUPPLEMENT TO PREVENT NEURAL TUBE DEFECTS

(71) Applicant: BOARD OF REGENTS, THE UNIVERSITY OF TEXAS SYSTEM, Austin, TX (US)

(72) Inventors: Dean R. Appling, Austin, TX (US); Jessica E. Momb, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/912,044

(22) PCT Filed: Aug. 13, 2014

(86) PCT No.: PCT/US2014/050917
§ 371 (c)(1),
(2) Date: Feb. 12, 2016

(87) PCT Pub. No.: WO2015/023767
PCT Pub. Date: Feb. 19, 2015

(65) Prior Publication Data
US 2016/0193164 A1 Jul. 7, 2016

Related U.S. Application Data

(60) Provisional application No. 61/866,331, filed on Aug. 15, 2013.

(51) Int. Cl.
A61K 31/519 (2006.01)
A61P 25/28 (2006.01)
A61P 25/00 (2006.01)
A61P 3/02 (2006.01)
A23L 1/302 (2006.01)
A61K 31/19 (2006.01)
A61K 9/00 (2006.01)
A61K 45/06 (2006.01)
A61K 31/14 (2006.01)
A61K 31/714 (2006.01)
A61K 33/26 (2006.01)
C12N 15/86 (2006.01)
A23K 20/174 (2016.01)
A23K 20/24 (2016.01)
A23L 7/117 (2016.01)
A23L 33/15 (2016.01)
A23L 33/16 (2016.01)

(52) U.S. Cl.
CPC ............ *A61K 31/19* (2013.01); *A23K 20/174* (2016.05); *A23K 20/24* (2016.05); *A23L 7/117* (2016.08); *A23L 33/15* (2016.08); *A23L 33/16* (2016.08); *A61K 9/00* (2013.01); *A61K 31/14* (2013.01); *A61K 31/519* (2013.01); *A61K 31/714* (2013.01); *A61K 33/26* (2013.01); *A61K 45/06* (2013.01); *C12N 15/86* (2013.01); *C12N 2760/00043* (2013.01); *C12N 2760/00051* (2013.01); *C12N 2770/00043* (2013.01); *C12N 2770/00051* (2013.01)

(58) Field of Classification Search
CPC ...... A23L 33/15; A61K 31/519; A61K 31/714
See application file for complete search history.

(56) References Cited

U.S. PATENT DOCUMENTS

| | | | |
|---|---|---|---|
| 5,350,851 A | 9/1994 | Bailey et al. | |
| 5,997,915 A | 12/1999 | Bailey et al. | |
| 6,011,040 A | 1/2000 | Muller et al. | |
| 6,441,168 B1 | 8/2002 | Muller et al. | |
| 6,528,542 B2 | 3/2003 | Deluca et al. | |
| 6,808,725 B2 | 10/2004 | Bailey et al. | |
| 6,921,754 B2 | 7/2005 | Hahnlein et al. | |
| 7,850,992 B2 | 12/2010 | Deluca et al. | |
| 7,947,662 B2 | 5/2011 | Valoti et al. | |
| 2002/0052374 A1* | 5/2002 | Rabelink | A61K 31/495 514/250 |
| 2005/0037065 A1 | 2/2005 | Kirschner et al. | |
| 2005/0214383 A1* | 9/2005 | Bubnis | A61K 31/355 424/641 |
| 2006/0251722 A1* | 11/2006 | Bandak | A61K 9/2081 424/472 |
| 2008/0254098 A1* | 10/2008 | Ehrlich | A61F 13/2051 424/431 |
| 2009/0068190 A1* | 3/2009 | Bortz | A61K 31/10 424/141.1 |
| 2011/0008464 A1 | 1/2011 | Scott, III | |
| 2013/0164311 A1 | 6/2013 | DeCarlo et al. | |

FOREIGN PATENT DOCUMENTS

WO 1997027764 A1 8/1997

OTHER PUBLICATIONS

Altaweel MM, Hanzlik RP, Ver Hoeve JN, Eells J, Zhang B. Ocular and systemic safety evaluation of calcium formate as a dietary supplement. J Ocul Pharmacol Ther. Jun. 2009;25(3):223-30.

Hanzlik RP, Fowler SC, Eells JT. Absorption and elimination of formate following oral administration of calcium formate in female human subjects. Drug Metab Dispos. Feb. 2005;33(2):282-6. Epub Nov. 16, 2004.

Momb J, Lewandowski JP, Bryant JD, Fitch R, Surman DR, Vokes SA, Appling DR. Deletion of Mthfd1l causes embryonic lethality and neural tube and craniofacial defects in mice. Proc Natl Acad Sci U S A. Jan. 8, 2013;110 (2):549-54.

International Search Report and Written Opinion issued in related International Application No. PCT/US2014/050917 dated Nov. 19, 2014.

(Continued)

Primary Examiner — Tracy Liu
(74) Attorney, Agent, or Firm — Meunier Carlin & Curfman LLC

(57) ABSTRACT

Compositions and method for treating a folate-resistant disease in a subject are disclosed. The methods involve administering to the subject an effective amount of a composition containing a formate. For example, the method can be used to reducing the risk of neural tube defects during pregnancy. The method can also be used to treat other conditions normally treatable by folate supplementation.

8 Claims, 6 Drawing Sheets

(56) References Cited

OTHER PUBLICATIONS

Chanarin et al: "Vitamin B12 Regulates Folate Metabolism by the Supply of Formate", The Lancet, vol. 316, No. 8193, Sep. 1, 1980, pp. 505-508.
Sokoro A A H et al: "Formate pharmacokinetics during formate administration in folate-deficient young swine", Metabolism, Clinical and Experimental, W.B. Saunders Co., Philadelphia, PA, US, vol. 57, No. 7, Jul. 1, 2008, pp. 920-926.
Ross ME (2010) Gene-environment interactions, folate metabolism and the embryonic nervous system. Wiley Interdiscip Rev Syst Biol Med 2:471-480.
Hibbard ED & Smithells RW (1965) Folic Acid Metabolism and Human Embryopathy. Lancet 1:1254.
Hobbs CA, et al. (2010) Folate in Health and Disease, ed Bailey LB (CRC Press, Taylor & Francis Group, Boca Raton, FL), 2nd Ed, pp. 133-153.
Remington's Pharmaceutical Sciences, 20th ed., Lippincott Williams & Wilkins, Baltimore, MD, 2000, p. 704.
Moephuli SR, Klein NW, Baldwin MT, & Krider HM (1997) Effects of methionine on the cytoplasmic distribution of actin and tubulin during neural tube closure in rat embryos. Proc. Natl. Acad. Sci. U. S. A. 94:543-548.
Copp AJ, Greene ND, & Murdoch JN (2003) The genetic basis of mammalian neurulation. Nat Rev Genet 4:784-793.
Parle-McDermott A, et al. (2009) A common variant in MTHFD1L is associated with neural tube defects and mRNA splicing efficiency. Hum. Mutat. 30:1650-1656.
Remington's Pharmaceutical Sciences, 18th Ed. 1990 (Mack Publishing Co. Easton PA. 18042) at Chapter 89.
Marshall, K In: Modern Pharmaceutics Edited by G. S. Banker and C. T. Rhodes Chapter 10, 1979.
Lakso M, et al. (1996) Efficient in vivo manipulation of mouse genomic sequences at the zygote stage. Proc. Natl. Acad. Sci. U. S. A. 93:5860-5865.
Stratman JL, Barnes WM, & Simon TC (2003) Universal PCR genotyping assay that achieves single copy sensitivity with any primer pair. Transgenic Res. 12:521-522.
Pike ST, Rajendra R, Artzt K, & Appling DR (2010) Mitochondrial C1-THF synthase (MTHFD1L) supports flow of mitochondrial one-carbon units into the methyl cycle in embryos. J Biol Chem 285:4612-4620.
Prasannan P & Appling DR (2009) Human mitochondrial C1-tetrahydrofolate synthase: Submitochondrial localization of the full-length enzyme and characterization of a short isoform. Arch. Biochem. Biophys. 481:86-93.
Whiting J, et al. (1991) Multiple spatially specific enhancers are required to reconstruct the pattern of Hox-2.6 gene expression. Genes Dev. 5:2048-2059.
Green EL ed (1966) Biology of the Laboratory Mouse (Dover Publications, Inc., New York), 2nd Ed, p. 706.
Harris MJ & Juriloff DM (2007) Mouse mutants with neural tube closure defects and their role in understanding human neural tube defects. Birth Defects Res A Clin Mol Teratol 79:187-210.
Harris MJ & Juriloff DM (2010) An update to the list of mouse mutants with neural tube closure defects and advances toward a complete genetic perspective of neural tube closure. Birth Defects Res A Clin Mol Teratol 88:653-669.
Spiegelstein O, et al. (2004) Embryonic development of folate binding protein-1 (Folbp1) knockout mice: Effects of the chemical form, dose, and timing of maternal folate supplementation. Dev. Dyn. 231:221-231.
Beaudin AE, et al. (2011) Shmt1 and de novo thymidylate biosynthesis underlie folate-responsive neural tube defects in mice. Am. J. Clin. Nutr. 93:789-798.
Beaudin AE, et al. (2012) Dietary folate, but not choline, modifies neural tube defect risk in Shmt1 knockout mice. Am. J. Clin. Nutr. 95:109-114.
Narisawa A, et al. (2012) Mutations in genes encoding the glycine cleavage system predispose to neural tube defects in mice and humans. Hum Mol Gen 21:1496-1503.
Zhou X & Anderson KV (2010) Development of head organizer of the mouse embryo depends on a high level of mitochondrial metabolism. Dev. Biol. 344:185-195.
Beaudin AE, Perry CA, Stabler SP, Allen RH, & Stover PJ (2012) Maternal Mthfd1 disruption impairs fetal growth but foes not cause neural tube defects in mice. Am. J. Clin. Nutr. 95:882-891.
Tibbetts AS & Appling DR (2010) Compartmentalization of Mammalian folate-mediated one-carbon metabolism. Annu. Rev. Nutr. 30:57-81.
Christensen KE & Mackenzie RE (2008) Mitochondrial methylenetetrahydrofolate dehydrogenase, methenyltetrahydrofolate cyclohydrolase, and formyltetrahydrofolate synthetases. Vitam. Horm. 79:393-410.
Di Pietro E, Sirois J, Tremblay ML, & MacKenzie RE (2002) Mitochondrial NAD-Dependent Methylenetetrahydrofolate Dehydrogenase-Methenyltetrahydrofolate Cyclohydrolase is Essential for Embryonic Development. Mol Cell Biol 22:4158-4166.
Bolusani S, et al. (2011) Mammalian MTHFD2L Encodes a Mitochondrial Methylenetetrahydrofolate Dehydrogenase Isozyme Expressed in Adult Tissues. J. Biol. Chem. 286:5166-5174.
Herbert V & Zalusky R (1962) J. Clin. Invest. 41:1263-1276; Noronha JM & Silverman M (1962) Vitamin B12 and Intrinsic Factor, 2nd European Symposium, ed Heinrich HC (Verlag, Stuttgart), pp. 728-736.
Macfarlane AJ, et al. (2008) Cytoplasmic serine hydroxymethyltransferase regulates the metabolic partitioning of methylenetetrahydrofolate but is not essential in mice. J. Biol. Chem. 283:25846-25853.
Bai S, et al. (2005) DNA methyltransferase 3b regulates nerve growth factor-induced differentiation of PC12 cells by recruiting histone deacetylase 2. Mol Cell Biol 25:751-766.
Kobayakawa S, Miike K, Nakao M, & Abe K (2007) Dynamic changes in the epigenomic state and nuclear organization of differentiating mouse embryonic stem cells. Genes Cells 12:447-460.
Horswill MA, Narayan M, Warejcka DJ, Cirillo LA, & Twining SS (2008) Epigenetic silencing of maspin expression occurs early in the conversion of keratocytes to fibroblasts. Exp. Eye Res. 86:586-600.
Borgel J, et al. (2010) Targets and dynamics of promoter DNA methylation during early mouse development. Nat. Genet. 42:1093-1100.
Dunlevy LP, et al. (2006) Integrity of the methylation cycle is essential for mammalian neural tube closure. Birth Defects Res A Clin Mol Teratol 76:544-552.
Okano M, Bell DW, Haber DA, & Li E (1999) DNA methyltransferases Dnmt3a and Dnmt3b are essential for de novo methylation and mammalian development Cell 99:247-257.
Chang H, et al. (2011) Tissue-specific distribution of aberrant DNA methylation associated with maternal low-folate status in human neural tube defects. J Nutr Biochem 22:1172-1177.
Coelho CN & Klein NW (1990) Methionine and neural tube closure in cultured rat embryos: morphological and biochemical analyses. Teratology 42:437-451.

* cited by examiner

CALCIUM FORMATE AS A SUPPLEMENT TO PREVENT NEURAL TUBE DEFECTS

CROSS-REFERENCE TO RELATED APPLICATIONS

This application claims benefit of U.S. Provisional Application No. 61/866,331, filed Aug. 15, 2013, which is hereby incorporated herein by reference in its entirety.

STATEMENT REGARDING FEDERALLY SPONSORED RESEARCH OR DEVELOPMENT

This invention was made with Government Support under Grant Nos. GM086856 and HD074428 awarded by the National Institutes of Health. The Government has certain rights in the invention.

REFERENCE TO SEQUENCE LISTING

The Sequence Listing submitted Aug. 14, 2017, as a text file named "10046-045US1_ST25.txt," created on Aug. 14, 2017, and having a size of 2.36KB is hereby incorporated by reference pursuant to 37 C.F.R. §1.52 (e)(5).

BACKGROUND

Closure of the neural tube during development is a highly complex but poorly understood process. Not surprisingly, neural tube defects (NTDs) have a multifactorial etiology, including both genetic and environmental factors. The importance of maternal folate status to NTD risk was first suggested more than forty years ago (Hibbard ED & Smithells RW (1965) Lancet 1:1254). Many human studies show that periconceptional intake of supplemental folic acid can reduce the incidence of NTDs by as much as 70% in some populations (Ross ME (2010) Wiley Interdiscip Rev Syst Biol Med 2:471-480). These results led to mandated fortification of all enriched cereal grain products with folic acid in the U.S. beginning in 1996 to ensure that women of child-bearing age would consume adequate quantities of the vitamin. While folic acid fortification has decreased NTD incidence in some subpopulations, fortification has not completely eliminated NTDs (Hobbs C A, et al. (2010) Folate in Health and Disease, ed Bailey LB (CRC Press, Taylor & Francis Group, Boca Raton, Fla.), 2nd Ed, pp 133-153). Despite the strong clinical link between folate and NTDs, the biochemical mechanisms through which folic acid acts during neural tube development remain undefined.

SUMMARY

A method for treating a folate-resistant disease in a subject is disclosed that involves administering to the subject an effective amount of a composition containing a formate. For example, the method can be used to reduce the risk of neural tube defects during pregnancy. The method can also be used to treat other conditions normally treatable by folate supplementation. For example, the method can be used to treat hyperhomocysteinemia. In some cases, the subject being treated has a family history of neural tube defects. In some embodiments, the subject has been diagnosed with a folate deficiency, e.g., by a blood test. In some embodiments, the subject has been diagnosed with high plasma homocysteine, e.g., by a blood test. In some embodiments, the method involves administering to the subject an effective amount of a first composition containing a formate and a second composition containing a folate. In other embodiments, the method involves administering to the subject an effective amount of a composition containing both a formate and a folate. Therefore, also disclosed is a composition containing a formate, a folate, and a pharmaceutically or neutraceutically acceptable carrier. Also disclosed is a composition containing formate in a unit dose for prenatal supplementation.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A is an illustration of the Mthfd1l gene, comprising 28 exons, and encoding a protein with two domains. The catalytic domain begins in exon 10. Mice in which exon 5 was initially flanked by LoxP sites were crossed with the E2a-Cre line, producing offspring with complete recombination at the LoxP sites (grey arrowheads) and the resulting deletion of exon 5 and the neomycin phosphotransferase gene (Neo). Transcription from the endogenous Mthfd1l promoter produces a transcript containing exons 1-4 of Mthfd1l fused to an internal ribosome entry site (IRES) and the β-galactosidase gene (LacZ) followed by a polyadenylation site (pA). SA, splice acceptor site. FIG. 2B shows mouse genotyping by allele specific amplification. Mouse genomic DNA was subjected to allele specific amplification using a mixture containing F, R1 and R2 primers. A genomic fragment of 444 bp was amplified from the wild-type allele and a 324 bp fragment was amplified from the $Mthfd1l^z$ allele. FIG. 2C shows RT-PCR analysis of mRNA expressed in whole E11.5 embryos using primers f in exon 4 and r in exon 14, yielding a 1087 bp product. M, Mthfd1L; G, glyceraldehyde-3-phosphate dehydrogenase. FIG. 2D is an immunoblot of mitochondria isolated from whole E11.5 embryos. Each lane was loaded with 7 µg of total mitochondrial protein. Blots were probed with antibodies against MTHFD1L (M, 100 KDa) or the mitochondrial matrix marker, Hsp60 (H, 60 KDa).

FIG. 3C shows an embryo with completely open neural folds (craniorachischisis), indicated by the dashed lines. Note that the embryo curves to the left so the entire open neural tube is visible (arrowheads). FIG. 3D shows an embryo with exencephaly (arrowhead) and a wavy neural tube (magnified in FIG. 3E). FIG. 3F shows wild-type, 51 somite embryo showing normal facial development. FIG. 3G shows the same Mthfd1l$^{z/z}$ embryo (51 somites) imaged in 3D and 3E displaying facial defects. The maxillary processes (Ma) are globular, and are broadly separated from the midline (indicated by the frontonasal prominence, Fp). The mandibular processes (Md) in the Mthfd1l$^{z/z}$ embryo appears undergrown. Embryos in FIGS. 3D, 3E, and 3G are stained for β-galactosidase activity. Embryos in FIGS. 3A, 3B, 3C and 3D are all imaged at the same magnification (1.25×). Embryos in FIGS. 3F and 3G are at the same magnification (2×). The embryo in 3E is at 3.2× magnification.

FIGS. 4A and 4J show that Mthfd1l$^{z/+}$ embryos at approximately E10.5 and E11.5, respectively, exhibit regionalized β-galactosidase staining that is highest in the eyes, heart, limb and dorsal midline region. Dashed line in FIG. 4A indicates the level of all sections below, at 10× and 40× magnification. FIGS. 4B and 4K show that Mthfd1l$^{z/z}$ littermates of embryos in 4A and 4J, respectively, exhibit β-galactosidase staining that appears superficially ubiquitous. FIGS. 4D, 4G, 4L, and 4N show that sections through Mthfd1l$^{z/+}$ embryos have β-galactosidase activity in the basal area of the dorsal neuroepithelium while Mthfd1l$^{z/z}$ embryos (FIGS. 4E, 4H, 4M, 4O) have a smaller neural tube, kinks in the lumen, and a broader dorsal lumen. FIGS. 4C, 4F, and 4I show Mthfd1l gene expression visualized by in situ hybridization in a wholemount embryo (FIG. 4C) and a section through the same embryo (FIGS. 4F and 4I). Precise age of embryos: 4A=37 somites; 4B=34 somites; 4C=33 somites; 4J=44 somites; 4K=42 somites. The regions outlined by dashed boxes are magnified in the panels immediately below them. Embryos in FIGS. 4A, 4B, and 4C are imaged at 1.6×, and embryos 4J and 4K are imaged at 1.25×. Black arrowheads highlight areas of β-galactosidase staining or in situ hybridization.

DETAILED DESCRIPTION

Figure 1:
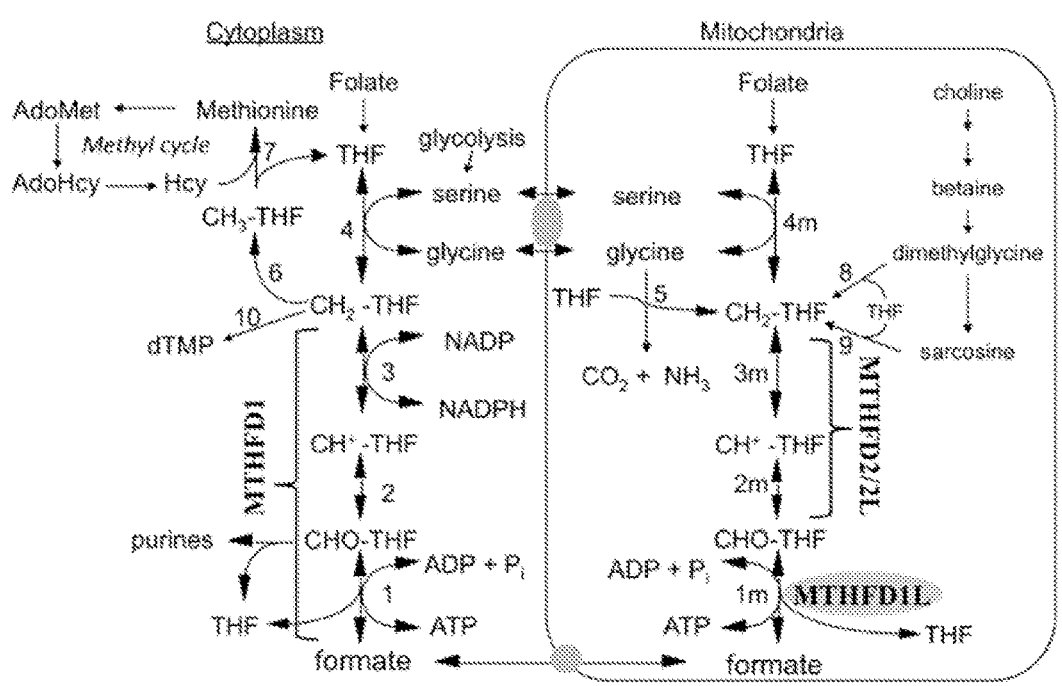
FIG. 1 is a schematic showing mammalian one-carbon metabolism. Reactions 1-4 are in both the cytoplasmic and mitochondrial (m) compartments. Reactions 1, 2, and 3, 10-formyl-THF synthetase, 5,10-methenyl-THF cyclohydrolase, and 5,10-methylene-THF dehydrogenase, respectively, are catalyzed by trifunctional $C_1$-THF synthase (MTHFD1) in the cytoplasm. In mammalian mitochondria, reaction 1 m is catalyzed by monofunctional MTHFD1L and reactions 2 m and 3 m by bifunctional MTHFD2 or MTHFD2L. The other reactions are catalyzed by the following: 4 and 4 m, serine hydroxymethyltransferase (SHMT); 5, glycine cleavage system (GCS); 6, 5,10-methylene-THF reductase; 7, methionine synthase; 8, dimethylglycine dehydrogenase; 9, sarcosine dehydrogenase; 10, thymidylate synthase. All reactions from choline to sarcosine are mitochondrial except the betaine to dimethylglycine conversion, which is cytoplasmic. Hcy, homocysteine; AdoHcy, S-adenosylhomocysteine; AdoMet, S-adenosylmethionine.

Disclosed are compositions and method based on the discovery that formate supplementation can protect against folate-resistant neural tube defects. Therefore, formate may be used to supplement or replace folic acid in subjects for whom folic acid treatment has proved insufficient or ineffective.

The term "folate-resistant" refers to a disease, such as a neural tube defect, that results from deficient or suboptimal folate one-carbon metabolism. Folic acid supplementation is not sufficient to treat or prevent these diseases.

The term "one-carbon metabolism" refers to the body's use of tetrahydrofolate (THF) as a 'carrier' of one-carbon units (i.e., $CO_2$, HCOOH, HCHO, $H_3COH$, $CH_4$) that are created by and needed for many crucial reactions that take place in the body. When folate is ingested, it is first converted to dihydrofolate, and then converted to THF. THF-mediated one-carbon metabolism is a metabolic network of interdependent biosynthetic pathways that is compartmentalized in the cytoplasm, mitochondria, and nucleus. One-carbon metabolism in the cytoplasm is required for the synthesis of purines and thymidylate and the remethylation of homocysteine to methionine. One-carbon metabolism in the mitochondria is required for the synthesis of formylated methionyl-tRNA; the catabolism of choline, purines, and histidine; and the interconversion of serine and glycine. Mitochondria are also the primary source of one-carbon units for cytoplasmic metabolism.

The term "folate deficiency" refers to inadequate levels of folate or one or more of its metabolites during one-carbon metabolism. Thus, this term refers to both a dietary deficiency and a metabolic deficiency.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

In some embodiments, the disclosed compositions and methods can be used to treat any disease characterized by folate deficiency, particularly those that are folate-resistant. Folate deficiency can occur when the body's need for folate is increased, when dietary intake of folate is inadequate, when the body excretes (or loses) more folate than usual, or when the body has deficient or suboptimal folate one-carbon metabolism. Patients with folate deficiencies can have formamino glutamate in their urine. This is an intermediate in the conversion of histadine to glutamate, which is THF dependent.

Situations that increase the need for folate include certain anemias, kidney dialysis, liver disease, malabsorption, including celiac disease, pregnancy and lactation (breast-feeding), tobacco smoking, and alcohol consumption. Medications that can interfere with folate utilization include anticonvulsant medications (such as phenytoin, and primidone), metformin (sometimes prescribed to control blood sugar in type 2 diabetes), methotrexate, an anti-cancer drug also used to control inflammation associated with Crohn's disease, ulcerative colitis and rheumatoid arthritis, sulfasalazine (used to control inflammation associated with Crohn's disease, ulcerative colitis and rheumatoid arthritis), triamterene (a diuretic), and oral contraceptives.

The disclosed methods can therefore be used to treat any folate deficiency condition treatable by folate supplementation. The disclosed methods can also be used to treat subject who has a limited ability to absorb or metabolize folic acid. Folate deficiencies (along with deficiencies in vitamin B6 and vitamin B12) can lead to many medical conditions, including glossitis (chronic inflammation of the tongue), diarrhea, depression, confusion, anemia, fetal neural tube defects and brain defects (during pregnancy), cardiovascular disease, and hyperhomocysteinemia. Hyperhomocysteinemia is characterized by abnormally high levels of homocysteine in the blood (e.g., above 15 µmol/L). Hyperhomocysteinemia is typically managed with vitamin B6, folic acid, and vitamin B12 supplementation. Therefore, in some embodiments, the disclosed compositions comprising formate may be used to treat a subject with hyperhomocysteinemia.

The formate of the disclosed compositions and methods can be formic acid (methanoic acid) or a pharmaceutically acceptable salt or ester thereof. Pharmaceutically acceptable salts are known in the art, and can be prepared using standard methods. See, for example, Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002. Pharmaceutically acceptable salt can include alkali metal salts, including sodium or potassium salts; alkaline earth metal salts, e.g., calcium or magnesium salts; and salts formed with suitable organic ligands, e.g., quaternary ammonium salts. Examples of suitable formate salts include calcium formate, sodium formate, ammonium formate, potassium formate, magnesium formate, and combinations thereof. In a preferred embodiment, the formate is calcium formate.

The folate of the disclosed compositions and methods can be folic acid (pteroyl-L-glutamic acid), a bioactive derivative thereof (e.g., a reduced form of folic acid), or a pharmaceutically acceptable salt or ester thereof. Folic acid (also referred to as folate, vitamin M, vitamin B9, vitamin Bc (or folacin), and pteroyl-L-glutamate) is a form of the water-soluble vitamin B9. Chemically, folic acid is a tripartite molecule containing a pterin moiety, a para-aminobenzoic acid moiety, and a γ-linked glutamate residue, as shown below.

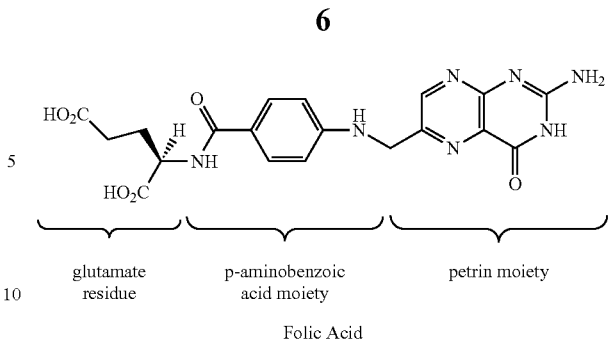

Folic Acid

Upon administration, folic acid is enzymatically converted to a biologically active folate in vivo. Therefore, formulations containing, for example, both a reduced folate and folic acid, may have the benefit of providing both a readily available biologically active folate as well as a longer term source of a biologically active folate (e.g., folic acid).

The folate can be a natural folate, such as levomefolic acid (also known as 5-MTHF, methylfolate, or 5-methyltetrahydrofolate), or a pharmaceutically acceptable salt or ester thereof. In some embodiments, the folate is L-methylfolate (also known as L-5-methyltetrahydrofolate (L-5-MTHF), which is a metabolically active form of folate).

In some embodiments, the folate is a reduced folate (e.g., folinic acid), or a natural isomer of a reduced folate. Suitable reduced folates are known in the art, and described, for example, in U.S. Pat. Nos. 5,350,851, 5,997,915, and 6,808,725 to Bailey et al.; U.S. Pat. Nos. 6,011,040 and 6,441,168 to Muller et al.; and U.S. Pat. No. 6,921,754 to Hahnlein et al.

The folate can be one or more natural isomers of reduced folate, one or more synthetic isomers of reduced folate, or combinations thereof. In formulations containing both natural and synthetic isomers of reduced folate, the natural and synthetic folates may be incorporated in equal molar ratios, or different molar ratios.

Natural isomers of reduced folates are described in WO 1997027764 A1, which is hereby incorporated by reference for the teaching of these natural isomers of reduced folates. Natural isomers of suitable reduced folate include, but are not limited to, (6S)-tetrahydrofolic acid, 5-methyl-(6S)-tetrahydrofolic acid, 5-formyl-(6S)-tetrahydrofolic acid, 10-formyl-(6R)tetrahydrofolic acid, 5,10-methylene-(6R)-tetrahydrofolic acid, 5,10-methenyl-(6R)tetrahydrofolic acid, and 5-formimino-(6S)-tetrahydrofolic acid. Other natural isomers of reduced folate include the polyglutamyls, such as the diglutamyl, triglutamyl, tetraglutamyl, pentaglutamyl, and hexaglutamyl, derivatives of (6S)-tetrahydrofolic acid, 5-methyl-(6S)tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, and 5-formimino-(6S)-tetrahydrofolic acid.

Synthetic isomers of reduced folate include, but are not limited to, (6R)-tetrahydrofolic acid, 5-methyl-(6R)-tetrahydrofolic acid, 5-formyl-(6S)-tetrahydrofolic acid, 10-formyl-(6S)tetrahydrofolic acid, 5,10-methylene-(6S)-tetrahydrofolic acid, 5,10-methenyl-(6S)tetrahydrofolic acid, 5-formimino-(6R)-tetrahydrofolic acid, and polyglutamyl derivatives thereof.

Any or all of the natural and synthetic isomers of reduced folate can be present as a single enantiomer or a mixture of enantiomers and/or diastereomers. The reduced folates can be either amorphous or crystalline. In certain embodiments, the reduced folate is in an amorphous state. In other embodiments, the reduced folate is crystalline. In still other embodiments, the one or more reduced folates are a mixture of amorphous and crystalline materials.

The folate can be a pharmaceutically acceptable salt of any of the folates described above. Pharmaceutically acceptable salts of folates include derivatives of folates wherein the parent folate is modified by making the acid-addition or base-addition salt thereof. Example of pharmaceutically acceptable salts include but are not limited to mineral or organic acid salts of basic residues such as amines; and alkali or organic salts of acidic residues such as carboxylic acids.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

In certain embodiments, the folate salt is a glucosamine salt of a folate (e.g., a glucosamine salt of a reduced folate), a galactosamine salt of a folate (e.g., a galactosamine salt of a reduced folate), or combinations thereof. Examples of suitable glucosamine and galactosamine salts include D-glucosamine dihydrofolate and D-glucosamine tetrahydrofolate, unsubstituted or substituted with a 5-methyl-, 5-formyl-, 10-formyl-, 5,10-methylene-, 5,10-methenyl moiety; and D-galactosamine dihydrofolate and D-galactosamine tetrahydrofolate, unsubstituted or substituted with a 5-methyl-, 5-formyl-, 10-formyl-, 5,10-methylene-, 5,10-methenyl moiety, wherein the reduced folates exhibit a (6R,S), (6S), or (6R) configuration. Suitable glucosamine and galactosamine salts of reduced folates are known in the art, and described in U.S. Pat. No. 7,947,662 to Valoti, et al., which is incorporated herein by reference.

In certain embodiments, the folate comprises D-glucosamine (6R,S)-tetrahydrofolate, D-glucosamine (6S)-tetrahydrofolate, D-glucosamine (6R)-tetrahydrofolate; D-galactosamine (6R,S)-tetrahydrofolate, D-galactosamine (6S) tetrahydrofolate, D-galactosamine (6R)tetrahydrofolate; D-glucosamine 5-methyl-(6R,S)-tetrahydrofolate, D-glucosamine 5-methyl(6S)-tetrahydrofolate, D-glucosamine 5-methyl-(6R)-tetrahydrofolate; D-galactosamine 5-methyl (6R,S)-tetrahydrofolate, D-galactosamine 5-methyl-(6S)-tetrahydrofolate, D-galactosamine 5-methyl-(6R)-tetrahydrofolate, or combinations thereof. In a preferred embodiment, the folate comprises D-glucosamine 5-methyl-(6S)-tetrahydrofolate (also known as N-[4-[[[(6S)-2-amino-1,4,5,6,7,8-hexahydro-5-methyl-4-oxo-6-pteridinyl]methyl]amino]benzoyl]-L-glutamic acid, glucosamine salt).

The disclosed compositions can optionally contain one or more additional vitamins, minerals, other nutraceuticals, or combinations thereof. The disclosed compositions can optionally include vitamin A. Vitamin A can be provided in any suitable form for administration, including as a retinyl ester (e.g., retinyl acetate or palmitate), alpha-carotene, beta-carotene, gamma-carotene, beta-cryptoxanthin, and combinations thereof. The disclosed compositions can optionally contain vitamin $B_1$ (thiamine) or a derivative thereof. Derivatives of vitamin $B_1$ include compounds formed from vitamin $B_1$ that are structurally distinct from vitamin $B_1$, but retain the active function of vitamin $B_1$, such as allithiamine, prosultiamine, fursultiamine, benfotiamine, sulbutiamine, and combinations thereof. The disclosed compositions can optionally contain vitamin $B_2$ (riboflavin) or a derivative thereof. Derivatives of vitamin $B_2$ include compounds formed from vitamin $B_2$ that are structurally distinct from vitamin $B_2$, but retain the active function of vitamin $B_2$. The disclosed compositions can optionally contain vitamin $B_6$ (pyridoxine) or a derivative thereof. Derivatives of vitamin $B_6$ include compounds formed from vitamin $B_6$ that are structurally distinct from vitamin $B_6$, but retain the active function of vitamin $B_6$. Examples of suitable forms of B6 that can be incorporated into the pharmaceutical formulations include pyridoxine, pyridoxine 5'-phosphate, pyridoxal, pyridoxal 5'-phosphate, pyridoxamine, pyridoxamine 5'-phosphate, and combinations thereof. The disclosed compositions can optionally contain vitamin $B_{12}$ (cobalamin) or a derivative thereof. Examples of suitable forms of vitamin $B_{12}$ include, but are not limited, to cyanocobalamin, hydroxocobalamin, nitrocobalamin, methylcobalamin, deoxyadenosylobalamin, adenosylcobalamin, and combinations thereof. The disclosed compositions can optionally contain pantothenic acid (also known as vitamin $B_5$) or a derivative or salt thereof (such as calcium pantothenate). Derivatives of pantothenic acid include compounds formed from pantothenic acid that are structurally distinct from pantothenic acid, but retain the active function of pantothenic acid. The disclosed compositions can optionally contain biotin (also known as vitamin $B_7$ and vitamin H) or a derivative thereof. Derivatives of biotin include compounds formed from biotin that are structurally distinct from biotin, but retain the active function of biotin. The disclosed compositions can optionally contain vitamin $B_3$ (niacin) or derivatives thereof, such as niacinamide. Derivatives of vitamin $B_3$ include compounds formed from vitamin $B_3$ that are structurally distinct from vitamin $B_3$, but retain the active function of vitamin $B_3$. The disclosed compositions can optionally contain vitamin C (ascorbic acid) or a salt or derivative thereof (such as sodium ascorbate). Derivatives of vitamin C include compounds formed from vitamin C that are structurally distinct from vitamin C, but retain the active function of vitamin C. The disclosed compositions can optionally contain vitamin $D_3$ (cholecalciferol) or a derivative thereof. Derivatives of vitamin $D_3$ include compounds formed from vitamin $D_3$ that are structurally distinct from vitamin $D_3$, but retain the active function of vitamin $D_3$. The disclosed compositions can optionally contain vitamin E (dl-α-tocopheryl acetate) or a derivative thereof. Derivatives of vitamin E include compounds formed from vitamin E that are structurally distinct from vitamin E, but retain the active function of vitamin E. The disclosed compositions can optionally contain vitamin K (phylloquinone) or a derivative thereof. Derivatives of vitamin K include compounds formed from vitamin K that are structurally distinct from vitamin K, but retain the active function of vitamin K.

The disclosed compositions can optionally contain one or more additional minerals. For example, the disclosed compositions can optionally contain a suitable source of zinc, such as a biocompatible zinc salt (e.g., zinc sulfate). The disclosed compositions can optionally contain an iron source, such as a biocompatible iron salt. Examples of suitable iron salts include, but are not limited to, ferrous sulfate, ferrous fumarate, ferrous succinate, ferrous gluconate, ferrous lactate, ferrous glutamate, ferrous glycinate, and combinations thereof. The disclosed compositions can optionally contain a suitable source of copper, such as a biocompatible copper salt (e.g., cupric oxide or cupric sulfate). The disclosed compositions can optionally contain a magnesium source, such as a biocompatible magnesium salt. Examples of suitable magnesium salts include, but are not limited to, magnesium stearate, magnesium carbonate, magnesium oxide, magnesium hydroxide, magnesium sulfate, and combinations thereof. The disclosed compositions can optionally contain a calcium source, such as a biocompatible calcium salt. Biologically-acceptable calcium compounds include, but are not limited to, calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and combinations thereof.

The disclosed compositions can optionally contain one or more additional nutraceutical agents, such as proteins, carbohydrates, amino acids, fatty acids, antioxidants, plant or animal extracts, or combinations thereof. Exemplary nutraceutical agents and dietary supplements are disclosed, for example, in Roberts et al., (*Nutriceuticals: The Complete Encyclopedia of Supplements, Herbs, Vitamins, and Healing Foods*, American Nutriceutical Association, 2001). Nutraceutical agents and dietary supplements are also disclosed in *Physicians' Desk Reference for Nutritional Supplements*, 1st Ed. (2001) and *The Physicians' Desk Reference for Herbal Medicines*, 1st Ed. (2001). In some cases, the disclosed compositions may contain one or more amino acids. Examples of suitable amino acids which can be incorporated into the pharmaceutical formulations include phenylalanine, valine, threonine, tryptophan, isoleucine, methionine, leucine, lysine, histidine, arginine, cysteine, glycine, glutamine, proline, serine, tyrosine, and combinations thereof. In some cases, the disclosed compositions may contain one or more botanic extracts. Examples of suitable botanic extracts include leucocyanidins, ginkgo biloba, ginseng, green tea, valerian, passion flower, chamomile, aloe vera, green tea, guggul, and combinations thereof. In some embodiments, the disclosed compositions may contain one or more fatty acids, omega-3 fatty acids, omega-6 fatty acids, omega-9 fatty acids, phospholipids, or combinations thereof. Alpha-linolenic (ALA), docosahexaenoic (DHA), and eicosapentaenoic (EPA) acids are examples of omega-3 fatty acids. Linoleic acid (LA) and arachidonic acid (AA) are examples of omega-6 fatty acids. Oleic (OA) and erucic acid (EA) are examples of omega-9 fatty acids. Other suitable nutraceuticals that can be optionally incorporated into the pharmaceutical/nutraceutical formulations described herein include lutein, phosphatidylserine, lipoic acid, melatonin, glucosamine, chondroitin, lycopene, whole foods, food additives, herbs, phytonutrients, antioxidants, flavonoid constituents of fruits, fish and marine animal oils (e.g. cod liver oil), probiotics (e.g., lactobacilli, spores, yeasts, and combinations thereof), S-Adenosyl methionine (SAMe), ubiquinone, choline, and combinations thereof.

In some embodiments, the method involves administering to the subject an effective amount of a first composition containing a formate and a second composition containing a folate. For example, the first composition and the second composition can be administered within about 0 to 12 hours of each other, including about 0, 0.5, 1, 2, 3, 4, 5, 6, 7, 8, 9, 10, 11 or 12 hours of each other. In other embodiments, the method involves administering to the subject an effective amount of a composition containing both a formate and a folate. Therefore, also disclosed is a composition containing a formate, a folate, and a pharmaceutically or nutraceutically acceptable carrier.

The formate is preferably present in the composition, and/or administered to the subject, in an amount that is about 100-100,000 times higher than the folate, including about 1,000 to about 50,000 times higher, or about 10,000 to about 50,000 higher. In some embodiments, the formate is administered in a daily dosage of about 1 mg/kg to about 1 g/kg, such as about 10 mg/kg to about 500 mg/kg, including about 10, 20, 30, 40, 50, 60, 70, 80, 90, 100, 150, 200, 250, 300, 350, 400, 450, or 500 mg/kg.

Also disclosed is a composition containing formate in a unit dose for prenatal supplementation. In some embodiments, the unit dose is a daily unit dose. In other embodiments, the dose is administered two to three times per day. Therefore, in some embodiments, the unit dose contains about 0.5 mg to about 100 g of the formate, such as about 100 mg to about 10 g, including about 100, 200, 300, 400, 500, 600, 700, 800, 900 mg, or about 1, 2, 3, 4, 5, 6, 7, 8, 9, or 10 g of the formate.

The unit dose can also contain about 100 µg to about 1.0 mg of folic acid, such as about 400 µg to about 800 µg of the folic acid. The unit dose can alternatively contain about 1 mg to about 100 mg of L-methylfolate, including about 15 mg L-methylfolate, of or a pharmaceutically acceptable salt thereof (e.g., L-methylfolate calcium (levomefolate calcium).

Disclosed are pharmaceutical/nutraceutical compositions containing therapeutically (or diagnostically) effective amounts of one or more folates and/or formates and a one or more pharmaceutically acceptable excipients. The term "pharmaceutically acceptable" and "neutraceutically acceptable" refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Pharmaceutical excipients suitable for administration of the folates and/or formates provided herein include any such excipients known to those skilled in the art to be suitable for the particular mode of administration. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

Pharmaceutical formulations can be formulated for any suitable mode of administration. In certain embodiments, the pharmaceutical formulation is formulated for enteral delivery. Examples of compositions for enteral consumption (enteral including oral, intragastric, or transpyloric), include oral solid dosage forms, food preparations, food supplements, essential nutrient preparations, and vitamin preparations. Oral solid dosage forms are known in the art, and described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules. A description of possible solid dosage forms for is given by Marshall, K. In: Modern Pharmaceutics Edited by G. S. Banker and C. T. Rhodes Chapter 10, 1979.

Examples of suitable food or vitamin preparations include those to which folic acid is currently added for use by either humans or other animals. More specifically, these compositions are, but are not limited to, multivitamin (with or without minerals and other nutrients) preparations (such preparations can be in solid, liquid or suspension forms); breakfast foods such as prepared cereals, breakfast drink mixes, toaster pastries and breakfast bars; infant formulas; dietary supplements and complete diet and weight-loss formulas and bars; animal feed or animal feed supplements (for example, for poultry), and pet foods. The disclosed compositions can also be used in a vitamin formulation containing at least one other vitamin (for example another vitamin such as a B vitamin) other than ascorbic acid (vitamin C), although ascorbic acid can be an additional component. Such nutrients or vitamins can be those intended for either human or animal use. Other ingredients may also be present, such as fillers, binding agents, stabilizers, sweeteners, including nutitive sweeteners (e.g. sucrose, sorbitol and other polyols) and nonnutritive sweeteners (e.g. saccharin, aspartame, and acesulfame K), colorants, flavors, buffers, salts, coatings, and the like that are known to those skilled in the art of vitamin formulation.

Formulations containing folates and/or formates can be administered as a medicament or a nutritional supplement. In certain embodiments, the formulations are administered to a female who is pregnant, a female who is attempting to become pregnant, a female who has had a miscarriage, or a female who has carried a fetus having a neural tube defect, a cleft lip defect, and/or a cleft palate defect.

In some cases, the formulations are administered to a subject who has a limited ability to absorb or metabolize folic acid. In some cases, the formulations are administered to a subject who possesses one or more mutations in 10-methylenetetrahydrofolate reductase (MTHFR), the enzyme that is responsible for conversion of folic acid to 5-methyltetrahydrofolate (5-MTHF). In particular embodiments, the subject is homozygous or heterozygous for a 677C→T polymorphism of methylenetetrahydrofolate reductase.

In some embodiments, the formulations are administered as a medicament, a food additive or a nutritional supplement, for the prevention and/or the treatment of neurological affliction such as, for instance, subacute encephalitis associated with dementia and vacuolar myelopathies; pathopsychological, vascular and cardiovascular such as, for instance premature occlusive arterial disease, severe vascular disease in infancy and childhood, progressive arterial stenosis, intermittent claudication, renovascular hypertension, ischemic cerebrovascular disease, premature retinal artery and retinal vein occlusion, cerebral occlusive arterial disease, occlusive peripheral arterial disease, premature death due to thromboembolic disease and/or ischemic heart disease; cancer; autoimmune diseases, such as, for instance, psoriasis, celiac disease, arthritic and inflammation conditions; megaloblastic anaemia due to folate deficiency, intestinal malabsorption, for maintaining and/or normalizing the homocysteine level and/or metabolism; alterations of the synthesis and/or the functioning and/or the changes of DNA and RNA and the alterations of cell synthesis; depressive illnesses; and combinations thereof.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Deletion of Mthfd1l Causes Embryonic Lethality and Neural Tube and Craniofacial Defects in Mice Folate-dependent one-carbon (1C) metabolism is highly compartmentalized in eukaryotes, and mitochondria play a critical role in cellular 1C metabolism. The cytoplasmic and mitochondrial compartments are metabolically connected by transport of 1C donors such as serine, glycine, and formate across the mitochondrial membranes, supporting a mostly unidirectional flow (clockwise in FIG. 1) of 1C units from serine to formate, and onto purines, thymidylate (dTMP), and methionine. It appears that under most conditions, the majority of 1C units for cytoplasmic processes are derived from mitochondrial formate. This formate is exported to the cytoplasm where it is reattached to tetrahydrofolate (THF) for use in de novo purine biosynthesis, or further reduced for either thymidylate synthesis or remethylation of homocysteine to methionine. The 1C unit interconverting activities represented in FIG. 1 by reactions 1-3 (and 1 m-3 m in mitochondria) are the central players in this intercompartmental pathway. These crucial reactions are catalyzed by members of the methylenetetrahydrofolate dehydrogenase (MTHFD) family in eukaryotes. The first member of this family to be characterized was the cytoplasmic MTHFD1 protein, a trifunctional enzyme possessing 10-formyl-THF synthetase, 5,10-methenyl-THF cyclohydrolase, and 5,10-methylene-THF dehydrogenase activities (reactions 1-3). This enzyme incorporates formate, released from mitochondria, into the cytoplasmic 1C THF pool as 10-formyl-THF (CHO-THF), which is required for de novo purine biosynthesis. MTHFD1 can also catalyze reduction of the 1C unit to 5,10-methylene-THF ($CH_2$-THF) for dTMP synthesis (reaction 10), or for methyl group biogenesis via 5-methyl-THF ($CH_3$-THF) (reaction 6). The MTHFD2 protein is a mitochondrial bifunctional $CH_2$-THF dehydrogenase/methenyl-THF cyclohydrolase (reactions 3 m, 2 m). Mitochondrial $CH_2$-THF dehydrogenase isozyme, encoded by the Mthfd2l gene, is bifunctional, possessing both $CH_2$-THF dehydrogenase and methenyl-THF cyclohydrolase activities (reactions 3 m, 2 m). The final step in the mammalian mitochondrial pathway to formate (reaction 1 m) is catalyzed by mitochondrial 10-formyl-THF synthetase, encoded by the Mthfd1l gene. Despite sharing 61% amino acid similarity with the cytoplasmic trifunctional MTHFD1, MTHFD1L is a monofunctional enzyme, possessing only the 10-formyl-THF synthetase activity (reaction 1 m). The Mthfd1l gene is expressed in most adult tissues, but at higher levels in spleen, thymus, brain, and placenta. The Mthfd1l gene is also expressed at all stages of mammalian embryogenesis and ubiquitously throughout the embryo but with localized regions of higher expression along the neural tube, the brain, craniofacial structures, limb buds, and the tail bud. Moreover, metabolic tracer experiments in mouse embryonic fibroblasts (MEFs) showed that more than 75% of 1C units that enter the cytoplasmic methyl cycle are mitochondrially derived. Thus, in both embryos and adults, MTHFD1L catalyzes production of formate from 10-formyl-THF, the last step in the flow of 1C units from mitochondria to cytoplasm.

To investigate the role of mitochondrial formate production during development, Mthfd1l knockout mice were analyzed. As disclosed herein, loss of MTHFD1L is lethal to developing embryos, causing fetal growth restriction and aberrant neural tube closure with 100% penetrance in embryos that develop past the point of neural tube closure. Although there are other folate-related mouse models that exhibit NTDs, the Mthfd1l knockout mouse is the first fully penetrant model that does not require feeding a folate-deficient diet to cause this phenotype. Moreover, maternal supplementation with sodium formate is shown herein to decrease the incidence of NTDs and partially rescue the growth defect in embryos lacking Mthfd1l. These results reveal the critical role of mitochondrial formate in mammalian development, providing a mechanistic link between folic acid and neural tube defects.

Methods

Figures 2A, 2B, 2C, 2D:
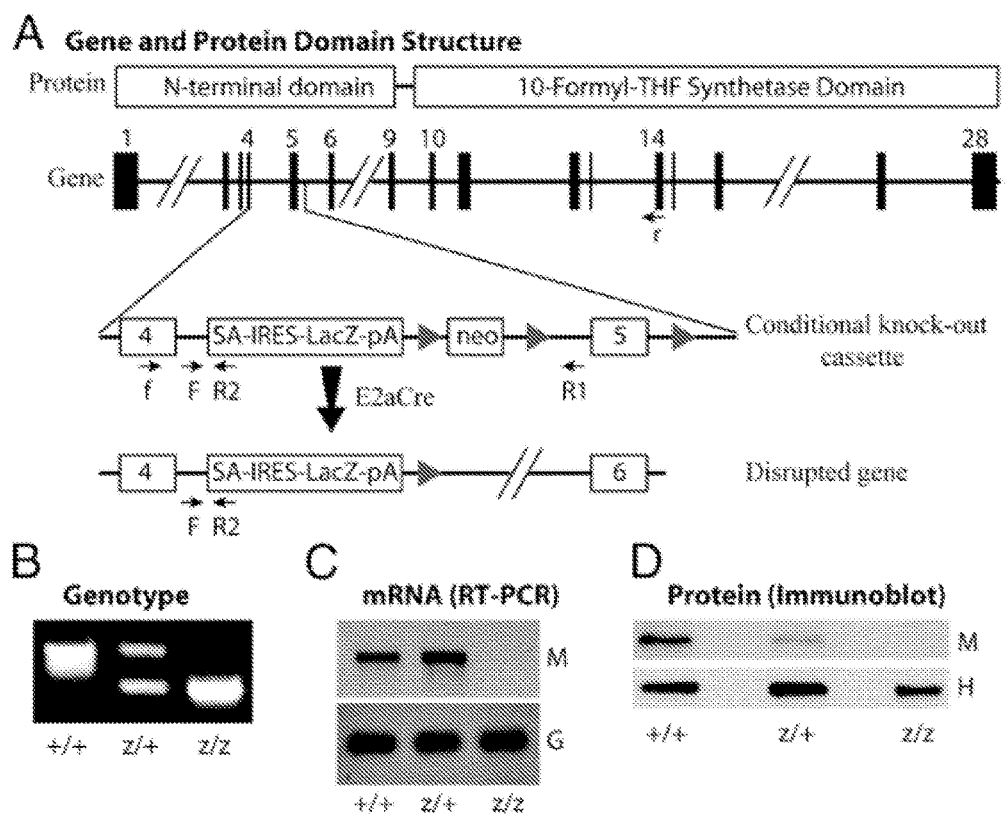
FIGS. 2A to 2D demonstrate that $Mthfd1l^{z/z}$ embryos do not produce detectable protein or full length transcripts.

Mice. All protocols used within this study were approved by the Institutional Animal Care and Use Committee of The University of Texas at Austin and conform to the National Institutes of Health Guide for the Care and Use of Laboratory Animals. All mice were maintained on a C57Bl/6 genetic background. Mice harboring a floxed conditional knockout cassette between exons 4 and 6 of Mthfd1l were obtained from the Wellcome Trust Sanger Institute (EUCOMM ID 37226). Mice carrying the floxed Mthfd1l allele were mated to mice expressing Cre recombinase under control of the E2a promoter (E2a-Cre) (Lakso M, et al. (1996) Proc. Natl. Acad. Sci. U.S.A 93:5860-5865) to generate heterozygous Mthfd1l$^{z/+}$ embryos lacking exon 5 and the neomycin resistance cassette (FIG. 2A). All mice were given ad libitum access to water and standard mouse chow (LabDiet 5K67).

Genotyping. Genotyping was carried out by a modified PCR method (Stratman JL, et al. (2003) Transgenic Res. 12:521-522). A mixture of three primers was used to detect the wild-type and/or recombined allele (FIG. 2A). To detect the wild-type allele, a forward primer (F) binding in the 5' region outside of the conditional cassette (5'-GAGTAT GTGAT TGCTT GGACC CCCAG GTTCC-3' (SEQ ID NO:1)) and a reverse primer (R1) binding 5' to exon 5 (5'-TGGCT CCCGA GGTTG TCTTC TGGCT ATGAT-3' (SEQ ID NO:2)) were employed. Amplification using these primers results in a 444 bp amplicon from the wild type allele. Amplification of the mutant allele uses the forward primer F, and a reverse primer (R2) complementary to a region only found in the gene-targeting cassette (5'-CGGCG CCAGC CTGCT TTTTT GTACA AACTT G-3' (SEQ ID NO:3)). Amplification using these primers results in a 324 bp amplicon in the presence of the mutant allele. See FIG. 2A for a schematic of primer binding sites used to detect Mthfd1l and Mthfd1l$^z$. Cre recombinase was detected using 5'-GCATT ACCGG TCGAT GCAAC GAGTG ATGAG-3' (SEQ ID NO:4) and 5'-GAGTG AACGA ACCTG GTCGA AATCA GTGCG-3' (SEQ ID NO:5) to produce a 408 bp amplicon, and SRY was detected using 5'-TTGTC TAGAG AGCAT GGAGG GCCAT GTCAA-3' (SEQ ID NO:6) and 5'-CCACT CCTCT GTGAC ACTTT AGCCC TCCGA-3' (SEQ ID NO:7) to detect a 273 bp amplicon.

Reverse Transcription-PCR (RT-PCR). Total RNA was prepared from Mthfd1l$^{+/+}$, Mthfd1l$^{z/+}$, and Mthfd1l$^{z/z}$ mouse embryos dissected at E11.5. First strand cDNA was synthesized using the SuperScript III First-Strand Synthesis System (Invitrogen) and random hexamers. PCR was performed using a forward primer f (5-CTCAC ATCTG CTTGC CTCCA-3' (SEQ ID NO:8)) binding in exon 4 and a reverse primer r (5'-ATGTC CCCAG TCAGG TGAAG-3' ((SEQ ID NO:9)) binding in exon 14 to amplify a 1087 bp amplicon from the wild-type transcript (see FIG. 2A for a schematic of primer binding sites). Primers amplifying a 115 bp amplicon (Forward: 5'-AGAGA CGGCC GCATC TTC-3' (SEQ ID NO:10), Reverse: 5'-CAAAT GGCAG CCCTG GTGA3' (SEQ ID NO:11)) from GAPDH were used as a positive control for cDNA quality.

Mitochondrial Isolation and Immunoblotting. Mitochondria were isolated from one embryo (Mthfd1l$^{+/+}$ and Mthfd1l$^{z/+}$) or three embryos (Mthfd1l$^{z/z}$) as previously described (Pike S T, et al (2010) J Biol Chem 285:4612-4620), except embryos were homogenized by pipetting. Protein concentration was determined by BCA assay (Thermo Fisher Scientific, Rockford, Ill.). Proteins were separated by SDS-PAGE and immunoblotted using rabbit polyclonal antiMTHFD1L (1:1000) (Prasannan P & Appling DR (2009) Arch. Biochem. Biophys. 481:86-93).

After incubation with HRP-conjugated goat anti-rabbit IgG (1:5000) (Invitrogen), reacting bands were detected using ECL Plus (GE Healthcare Life Sciences, Piscataway, N.J.). After stripping, blots were re-probed with rabbit polyclonal anti-Hsp60 (1:1000) (Enzo Life Sciences, Ann Arbor, Mich.).

Histology. Embryos were stained for β-galactosidase activity overnight as described previously (Whiting J, et al. (1991) Genes Dev. 5:2048-2059). Stained embryos were embedded in paraffin, sectioned at the level of the forelimb (four micrometer thickness) and counterstained with nuclear fast red. Mthfd1l wholemount in situ hybridization was performed using a riboprobe against the 3'UTR as previously described (Pike ST, et al (2010) J Biol Chem 285: 4612-4620). Embryos were then embedded in OCT medium and cryosectioned at the level of the forelimb (12 μm thickness).

Maternal Supplementation with Sodium Formate. Mthfd1l$^{z/+}$ matings were set up in a cage equipped with a water bottle containing either 0.37M or 0.55M sodium formate. The females had access to the supplemented water at least one day before observation of the plug. These concentrations were calculated to deliver either 5000 or 7500 mg sodium formate/kg/day, respectively, based on an average water intake of 5 mL per day for a 25 g C57BL/6 mouse (Green EL ed (1966) Biology of the Laboratory Mouse (Dover Publications, Inc., New York), 2nd Ed, p 706). The effect of formate supplementation was analyzed by a two-sided chi square test for NTD incidence and two-way ANOVA with Bonferroni post-test for crown-rump length.

Maternal Supplementation with Calcium Formate. Mthfd1l$^{z/+}$ matings were set up in a cage equipped with a water bottle containing 0.0096M, 0.019M, 0.056M or 0.096M calcium formate. The females had access to the supplemented water at least one day before observation of the plug. These concentrations were calculated to deliver 250, 500, 1500 or 2500 mg calcium formate/kg/day, respectively, based on an average water intake of 5 mL per day for a 25 g C57BL/6 mouse (Green EL ed (1966) Biology of the Laboratory Mouse (Dover Publications, Inc., New York), 2nd Ed, p 706). The effect of formate supplementation was analyzed by a two-tailed T-test for crown-rump length Results Mthfd1l is Essential in Mice.

Figures 3A, 3B, 3C, 3D, 3E, 3F, 3G:
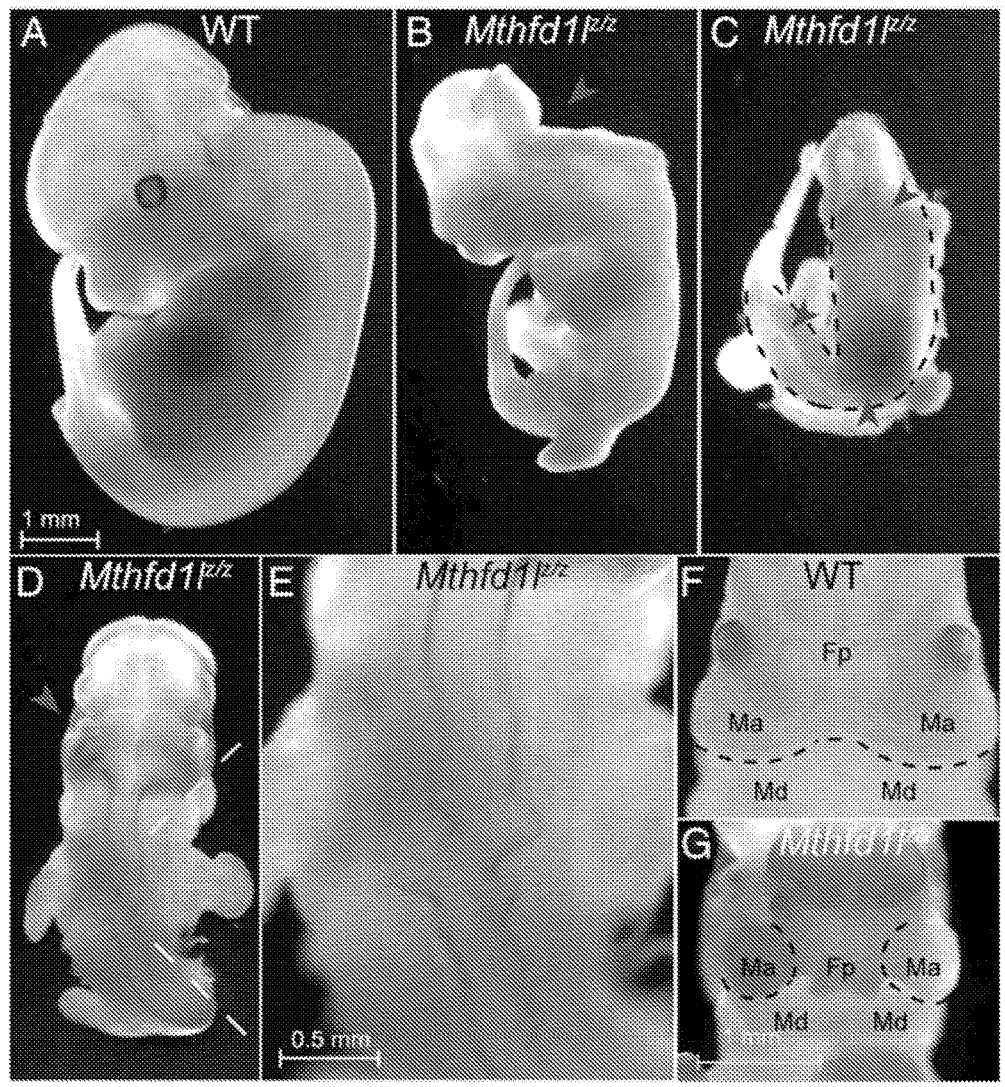
FIGS. 3A to 3G are images showing that $Mthfd1l^{z/z}$ embryos have neural tube and facial defects. Compared to wild-type E12.5 embryos (FIG. 3A), E12.5 $Mthfd1l^{z/z}$ biz embryos (FIGS. 3B-3E) exhibit a spectrum of neural tube defects including exencephaly (FIG. 3B, arrowhead).

A strain of conditional knockout ready Mthfd1l mice was obtained from the European Conditional Mouse Mutagenesis Program (EUCOMM). In this strain, the Mthfd1l locus is modified by the insertion of a cassette, containing a splice acceptor, internal ribosome entry site, the β-galactosidase gene (LacZ) followed by a polyadenylation signal, and the gene for neomycin phosphotransferase (Neo), between exons 4 and 6 of Mthfd1l (FIG. 2A). This allele has three LoxP sites: one between the polyadenylation signal and Neo, and two flanking exon 5. To generate a null allele, the mice were crossed to a Cre deleter strain, E2a-Cre (Lakso M, et al. (1996) Proc. Natl. Acad. Sci. U.S.A. 93:5860-5865). Recombination at the LoxP sites removes Neo and exon 5 to produce a disrupted allele containing LacZ followed by a polyadenylation signal (FIG. 2A). Transcription of the disrupted allele is expected to produce a transcript containing exons 1-4 spliced to LacZ. The disrupted Mthfd1l allele is designated as Mthfd1l$^z$. The genotype was confirmed by PCR (FIG. 2B) and RT-PCR analysis indicated that the wild-type Mthfd1l transcript is absent in Mthfd1l$^{z/z}$ embryos (FIG. 2C). Full-length MTHFD1L protein is undetectable in Mthfd1l$^{z/z}$ embryos (FIG. 2D), indicating that this is a likely null allele. No difference in growth from weaning to 5 weeks of age was observed between Mthfd1l$^{+/+}$ and Mthfd1l$^{z/+}$ mice. To determine the viability of homozygous null (Mthfd1l$^{z/z}$) mice, Mthfd1l$^{z/+}$ mice were intercrossed and the genotype distribution was determined (Table 1). A total of 172 weanlings from 31 litters were examined. The average litter size was 5.5 pups. The Mthfd1l genotypes were not distributed as expected for Mendelian inheritance of the nonfunctional Mthfd1l$^z$ allele. The ratio of Mthfd1l$^{+/+}$ to Mthfd1l$^{z/+}$ to Mthfd1l$^{z/z}$ was 55:117:0, indicating that the Mthfd1l$^{z/z}$ genotype causes embryonic lethality ($p=2.0\times10^{-11}$). If it is assumed that the Mthfd1l$^{z/z}$ genotype is lethal, Mthfd1l$^{+/+}$ and Mthfd1l$^{z/+}$ genotypes were observed in the expected frequency ($p=0.75$). Males and females were found at the expected frequencies, and Mthfd1l$^{z/+}$ mice appear healthy and breed normally.

resorption. The most common NTD phenotype was exencephaly with a wavy neural tube (FIG. 3D; n=11), or exencephaly alone (FIG. 3B, n=3). The most severe NTD observed was craniorachischisis (FIG. 3C; n=1). The nine Mthfd1l$^{z/z}$ embryos whose neural tubes had closed all displayed a wavy neural tube with a small, aberrantly formed head (FIG. 4B). In all, 20/24 Mthfd1l$^{z/z}$ embryos exhibited a wavy neural tube, and the earliest observation of this phenotype was at E9.5. The location of the waviness in the neural tube was variable, but most embryos exhibited a wavy neural tube beginning at approximately the same axis as the forelimb and extending caudally past the forelimb, as depicted in FIGS. 3D and 3E. Because many studies have noted an increased incidence of NTDs in females (Harris MJ & Juriloff DM (2007) Birth Defects Res A Clin Mol Teratol 79:187-210), E11.5-E12.5 Mthfd1l$^{z/z}$ embryos were genotyped for presence of the sex-receptor Y (SRY) locus. No bias was found for either sex [females n=6 (40%), males n=9 (60%), p=0.44].

In addition to aberrations in neural tube closure, facial deformities were also noted in Mthfd1l$^{z/z}$ embryos that were

TABLE 1

Mthfd1l nullizygous mice are not viable

| Genotype | Observed genotype distribution | | | Expected genotype distribution | | |
|---|---|---|---|---|---|---|
| | Male | Female | Total | Male | Female | Total |
| Mthfd1l$^{+/+}$ | 24 | 31 | 55 | 21.5 | 21.5 | 43 |
| Mthfd1l$^{z/+}$ | 56 | 61 | 117 | 43 | 43 | 86 |
| Mthfd1l$^{z/z}$ | 0 | 0 | 0 | 21.5 | 21.5 | 43 |
| Total embryos | 80 | 92 | 172 | 86 | 86 | 172 |
| Total litters observed | | | 31 | | | |
| Mean litter size (mean ± SD) | | | 5.5 ± 2.0 | | | |
| P value, observed vs. expected genotype distribution (1:2:1)* | | | 1.9994 × 10$^{-11}$ | | | |
| P value, observed vs. expected genotype distribution assuming embryonic lethality* | | | 0.7494 | | | |

*Analyzed by χ2 test.

Homozygous deletion of Mthfd1l results in delayed embryonic growth and defective neural tube closure. Since no Mthfd1l$^{z/z}$ pups were recovered at birth, the embryonic phenotype was invested. Embryos were dissected from pregnant dams at E8.5-E15.5, genotyped using yolk sac tissue, and their gross morphology was examined. All observed Mthfd1l$^{z/z}$ embryos exhibited a growth delay compared to wild-type and Mthfd1l$^{z/+}$ littermates. The severity of the developmental delay was variable, but on average the null embryos appeared to lag approximately 0.75 days behind their littermates. Some of the Mthfd1l$^{z/z}$ embryos died early during the gestational period, but all that survived past the point of neural tube closure (E9.5) exhibited aberrant neural tube phenotypes. Out of 152 embryos dissected at E11.5-E12.5, 52 Mthfd1l$^{+/+}$ embryos, 74 Mthfd1l$^{z/+}$ embryos, and 26 Mthfd1l$^{z/z}$ embryos were obtained, and 28 resorptions were observed. Of the 26 Mthfd1l$^{z/z}$ embryos, 15 exhibited a clear NTD phenotype (exencephaly or craniorachischisis) and 9 displayed a wavy neural tube phenotype (FIGS. 3B-3D). The remaining two Mthfd1l$^{z/z}$ embryos had completely open neural tubes but were not scored as having craniorachischisis because these embryos had failed to turn, suggesting that they may have been in the process of most apparent at the later stages. When compared to somite-matched wild-type or heterozygous embryos, E12.5 Mthfd1l$^{z/z}$ embryos display immature maxillary and mandibular processes (FIG. 3G). In Mthfd1l$^{z/z}$ embryos the maxillary processes of the first branchial arch appear globular and more widely separated than in somite-matched control embryos. In addition, the mandibular processes were undergrown (FIG. 3F,G; 7/7). No surviving Mthfd1l$^{z/z}$ embryos were observed after E12.5, preventing a later analysis of the phenotype.

Histological Analysis of Neural Tube Phenotypes.

Control (Mthfd1l$^{z/+}$) and Mthfd1l$^{z/z}$ embryos were sectioned and stained for β-galactosidase at E10.5 and E11.5. This allowed visualization of regionalized β-galactosidase activity, which should act as a reporter for Mthfd1l transcription (FIG. 2A). To confirm that the LacZ reporter recapitulated endogenous Mthfd1l gene expression, the patterns detected by β-galactosidase staining in Mthfd1l$^{z/+}$ sections were compared with endogenous Mthfd1l gene expression. Using in situ hybridization, transcript expression was observed in the ectoderm, underlying mesenchyme, and dorsal neural tube (FIGS. 4C, 4F, 4I). In the neural tube, the highest expression was detected in the basal surface of the dorsal neuroepithelium (FIG. 4F, arrowheads). β-galactosidase activity was more restricted in Mthfd1l$^{z/+}$ embryos (FIG. 4D), but was still seen within the same region of the neural tube as the gene expression pattern. It was conclude that the LacZ reporter partially recapitulates endogenous Mthfd1l gene expression with the difference most likely being due to reduced sensitivity.

Figures 4A, 4O:
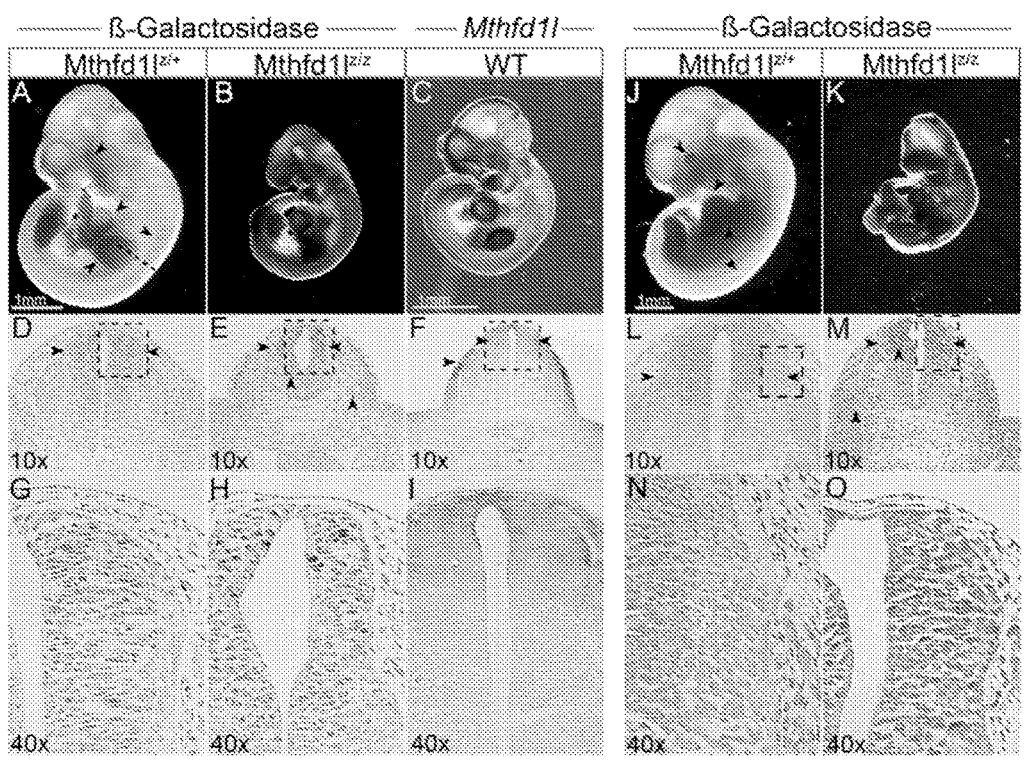
FIGS. 4A-4O are images showing aberrant neural tube morphology in Mthfd1l$^{z/z}$ embryos.

Mthfd1l$^{z/+}$ wholemount embryos stained for β-galactosidase activity have the highest levels in the eyes, heart, limb, and dorsal midline region (FIGS. 4A and 4J). In sectioned Mthfd1l$^{z/+}$ embryos, β-galactosidase activity was predominantly detected at the basal surface of the dorsal neuroepithelium, and was rarely detected in cells within and outside of the neural tube (FIG. 4D, 4G, 4L, 4N). In sectioned Mthfd1l$^{z/z}$ embryos, β-galactosidase activity was robustly detected both inside and outside the neural tube (FIGS. 4E, 4H, 4M, 4O). Similar to Mthfd1l$^{z/+}$ embryos, β-galactosidase was detected in the neuroepithelium; however, expression was less restricted dorsally in the nulls. In Mthfd1l$^{z/z}$ embryos with closed neural tubes, the morphology was abnormal throughout the neural tube in all embryos sectioned (E10.5 and E11.5, n=6). Neural tubes had abnormally shaped lumens, including asymmetric dorsal-lateral bulges as well as a broader dorsal lumen that were not seen in controls (FIGS. 4D, 4G, 4E, 4H, 4L-4O).

Dietary Supplementation with Sodium Formate.

Figures 5A, 5B, 5C, 5D:
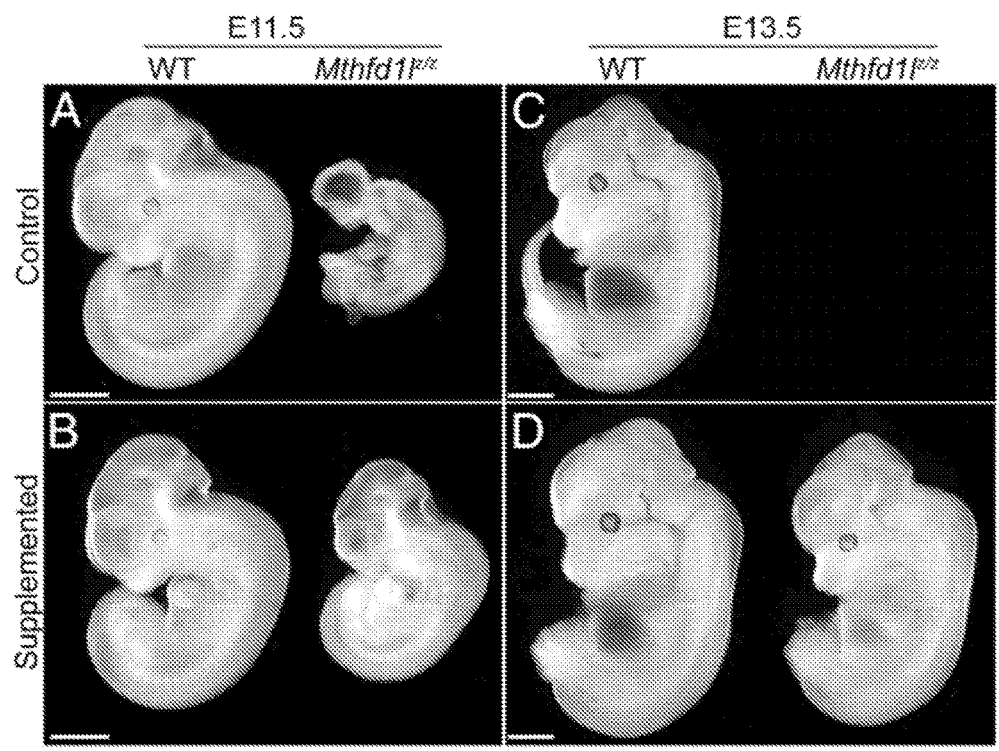
FIGS. 5A-5D show that maternal supplementation with sodium formate improves development and growth in Mthfd1l$^{z/z}$ embryos. Pregnant dams were administered a calculated dose of 7500 mg sodium formate/kg/day. Mthfd1l$^{z/z}$ embryos dissected at E11.5 (FIG. 5B) show improved growth compared to control embryos from unsupplemented dams (FIG. 5A). E13.5 embryos from unsupplemented (FIG. 5C) and supplemented (FIG. 5D) dams. Precise age of embryos: A=47 somites; B=36 somites; C=45 somites; D=41 somites. Scale bars correspond to 1.0 mm.

Because deletion of Mthfd1l is expected to result in loss of mitochondrial formate production, experiments were conducted to determine if maternal formate supplementation would improve development of Mthfd1l$^{z/z}$ embryos. Pregnant dams were given ad libitum access to water containing sodium formate to achieve a calculated dose of 5000 or 7500 mg sodium formate/kg/day; controls were given water without formate. As before, Mthfd1l$^{z/z}$ embryos were not recovered from unsupplemented dams (17 Mthfd1l$^{+/+}$, 34 Mthfd1l$^{z/+}$, 0 Mthfd1l$^{z/z}$ embryos, deviating significantly from the expected Mendelian ratio; p=0.0002). When dams were supplemented with 5000 mg/kg/day sodium formate, 4 Mthfd1l$^{+/+}$, 14 Mthfd1l$^{z/+}$, and 8 Mthfd1l$^{z/z}$ embryos were obtained from 3 litters between E15.5-18.5. This genotype distribution does not differ significantly from the expected Mendelian ratio (p=0.50), suggesting at least a partial rescue by formate. Next, the morphology of E10.5-E15.5 embryos from dams supplemented with 7500 mg/kg/day sodium formate was examined, obtaining 10 Mthfd1l$^{+/+}$ embryos, 31 Mthfd1l$^{z/+}$ embryos and 14 Mthfd1l$^{z/z}$ embryos from 6 litters, again conforming to the expected Mendelian ratio (p=0.48). Of the 14 Mthfd1l$^{z/z}$ embryos, 11 displayed normal neural tube closure and 3 had exencephaly (FIG. 5). Thus, compared to nulls from unsupplemented dams, formate supplementation at 7500 mg/kg/day gives a significantly higher frequency of nulls with normal neural tube closure (p=0.028). Importantly, 6 of the 14 Mthfd1l$^{z/z}$ embryos were dissected from dams at E13.5 or E15.5, whereas no surviving Mthfd1l$^{z/z}$ embryos were observed after E12.5 from unsupplemented dams. While supplemented versus non-supplemented embryos were not compared after E12.5 due to lethality of the unsupplemented embryos, formate supplementation partially rescued the growth defect in Mthfd1l$^{z/z}$ embryos (FIGS. 5A, 5B). The crown-rump length of formate supplemented Mthfd1l$^{z/z}$ E11.5 embryos was significantly greater than in unsupplemented Mthfd1l$^{z/z}$ embryos (5.0±0.1 vs. 3.6±0.3 mm respectively, p<0.01). Supplementation had no significant effect on crown-rump length of wild-type embryos (5.9±0.2 mm).

Dietary Supplementation with Calcium Formate

Table 2 shows that maternal supplementation with calcium formate improves development and growth in Mthfd1l$^{z/z}$ embryos. Pregnant dams were administered calculated doses of 250-2500 mg/kg/day. While Mthfd1l$^{z/z}$ embryos dissected at E15.5 are significantly smaller than wild-type and Mthfd1l$^{z/+}$ littermates, there is a dose-response effect, where an increase in growth is observed in Mthfd1l$^{z/z}$ embryos with increasing maternal calcium formate intake (Table 2).

TABLE 2

Maternal supplementation with calcium formate improves development and growth in Mthfd1l$^{z/z}$ embryos

| Genotype | Crown-rump length (cm) | | | | |
| --- | --- | --- | --- | --- | --- |
|  | 250 mg/kg | 500 mg/kg | 1500 mg/kg | 2500 mg/kg | 3500 mg/kg |
| Mthfd1l$^{+/+}$ | 1.39 + 0.1 | 1.32 + 0.17 | 1.46 + 0.2 | 1.43 + 0.07 | 1.34 + 0.2 |
| Mthfd1l$^{z/+}$ | 1.38 + 0.1 | 1.36 + 0.21 | 1.46 + 0.1 | 1.39 + 0.09 | 1.33 + 0.1 |
| Mthfd1l$^{z/z}$ | 1.05 + 0.1 | 1.03 + 0.06 | 1.17 + 0.13 | 1.20 + 0.04 | 1.1 + 0.2 |
| total Mthfd1l$^{z/z}$ embryos | 6 | 11 | 13 | 15 | 10 |
| number with facial defect | 4 | 8 | 4 | 0 | 3 |
| number with NTD | 2 | 0 | 1 | 5 | 1 |
| number of litters | 7 | 5 | 5 | 5 | 7 |
| CR length ttest, wt vs null | 6.30E−06 | 9.10E−005 | 0.00016 | 4.40E−010 | 0.013 |
| CR length ttest, wt vs het | 0.89 | 0.63 | 0.88 | 0.22 | 0.89 |
| null vs. null at 2500 mg/kg | 4.17E−06 | 2.46923E−08 | 0.544314488 | — | 0.064369727 |

Figure 6:
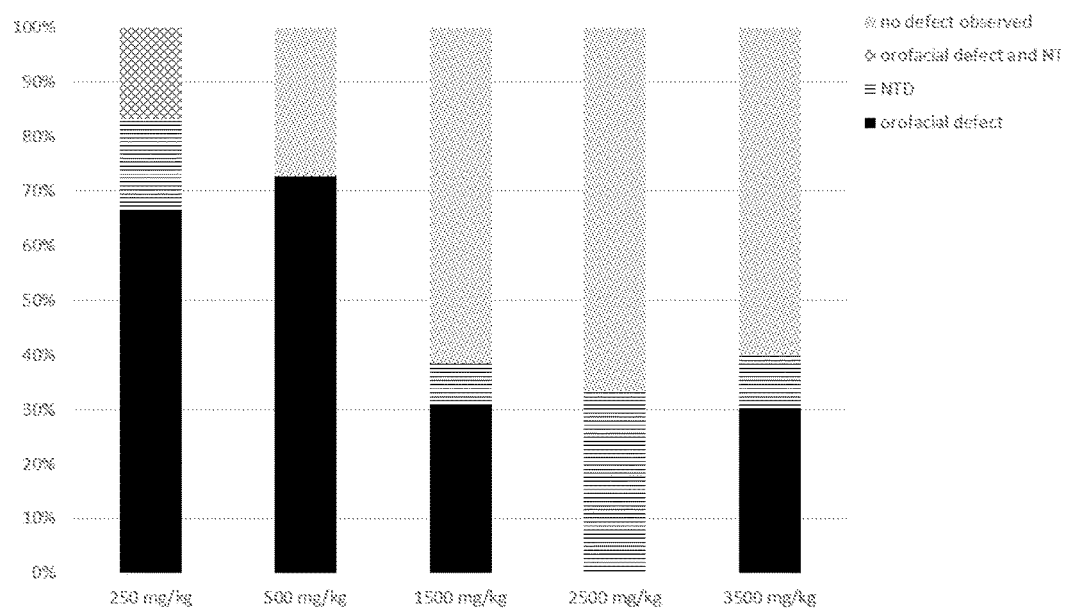
FIG. 6 is a bar graph showing calcium formate improves NTD and orofacial phenotypes in Mthfd1l$^{z/z}$ embryos.

As shown in Table 3 and FIG. 6, calcium formate improves NTD and orofacial defect phenotypes in a dose-dependent manner in the mouse model.

TABLE 3

Maternal supplementation with calcium formate improves NTD and orofacial phenotypes in Mthfd1l$^{z/z}$ embryos

|  | 250 mg/kg | 500 mg/kg | 1500 mg/kg | 2500 mg/kg | 3500 mg/kg |
|---|---|---|---|---|---|
| orofacial defect | 4 | 8 | 4 | 0 | 3 |
| NTD | 1 | 0 | 1 | 5 | 1 |
| orofacial defect and NTD | 1 | 0 | 0 | 0 | 0 |
| no defect observed | 0 | 3 | 8 | 10 | 6 |
| total Mthfd1l$^{z/z}$ embryos | 6 | 11 | 13 | 15 | 10 |
| *Orofacial/NTD Phenotype as a percentage* | | | | | |
| orofacial defect | 0.66666667 | 0.72727273 | 0.30769231 | 0 | 0.3 |
| NTD | 0.16666667 | 0 | 0.07692308 | 0.33333333 | 0.1 |
| orofacial defect and NTD | 0.16666667 | 0 | 0 | 0 | 0 |
| no defect observed | 0 | 0.27272727 | 0.61538462 | 0.66666667 | 0.6 |

Discussion

This study shows that all embryos lacking Mthfd1l exhibit aberrant neural tube closure including craniorachischisis and exencephaly and/or a wavy neural tube. The NTD phenotype (exencephaly and craniorachischisis) is accompanied by abnormal neural tube morphology characterized by asymmetric bulges in the neuroepithelium and a wider lumen in wavy areas of the neural tube. In addition to the NTD phenotype, Mthfd1l$^{z/z}$ embryos show immature maxillary and mandibular process development. Finally, maternal formate supplementation is shown to significantly reduce the incidence of NTDs, partially rescue the growth defect, and allow survival past the point of lethality seen in unsupplemented Mthfd1l$^{z/z}$ embryos. This knockout mouse is the first fully penetrant folate-pathway mouse model that does not require feeding a folate-deficient diet to cause these phenotypes. More than ten folate-related mouse mutants have been characterized thus far (Harris MJ & Juriloff DM (2010) Birth Defects Res A Clin Mol Teratol 88:653-669), but NTDs are observed in only three: Folr1, Shmt1 and Amt. Folr1 encodes folate receptor 1, one of the major folate transport systems, and homozygous knockout of Folr1 produces a severe folate deficiency in the embryo that can be rescued with maternal 5-formyl-THF supplementation (Spiegelstein O, et al. (2004) Dev. Dyn. 231:221-231). This rescue is "tunable", and depending on the dose of 5-formyl-THF administered to mothers during gestation, Folr1$^{-/-}$ embryos develop NTDs and orofacial deformities, or can be rescued to birth. Homozygous knockout of Shmt1, which encodes a cytoplasmic folate-metabolizing enzyme (FIG. 1, reaction 4), gives rise to a low frequency of NTDs in embryos from Shmt1$^{-/-}$ dams fed a folate-deficient diet (Beaudin AE, et al. (2011) Am. J. Clin. Nutr. 93:789-798; Beaudin AE, et al. (2012) Am. J. Clin. Nutr. 95:109-114). Amt encodes an aminomethyltransferase that is a subunit of the mitochondrially localized glycine cleavage system (GCS) which processes glycine to donate 1C units to THF, forming CH$_2$-THF (FIG. 1, reaction 5). Homozygous deletion of Amt is embryonic lethal, and Amt$^{-/-}$ embryos develop NTDs with 87% penetrance (Narisawa A, et al. (2012) Hum Mol Gen 21:1496-1503). The phenotype exhibited by the Amt knockout mouse suggests that the demand for 1C units is high during neurulation. This is consistent with the observation that maternal supplementation with methionine, which provides 1C units via the methyl cycle (FIG. 1), significantly improves neurulation in Amt null embryos while folic acid has no effect (Narisawa A, et al. (2012) Hum Mol Gen 21:1496-1503). The importance of the GCS to neural tube development is also supported by the occurrence of NTDs in the nehe mouse (Zhou X & Anderson KV (2010) Dev. Biol. 344:185-195). The nehe mouse carries a hypomorphic allele of lipoic acid synthetase, the mitochondrial enzyme that catalyzes the synthesis of lipoic acid, an essential cofactor for GCS and several other mitochondrial enzymes. One other folate pathway mouse model, targeting Mthfd1 (FIG. 1, cytoplasmic reactions 1-3), also displays disorganized neural tube closure in heterozygous Mthfd1$^{gt/+}$ embryos from Mthfd1$^{gt/+}$ dams fed a folate-deficient diet (Beaudin AE, et al (2012) Am. J. Clin. Nutr. 95:882-891). Although the defects in this model are not classic NTDs, they are reminiscent of the wavy neural tube phenotype observed in Mthfd1l$^{z/z}$ embryos.

The fact that Mthfd1l$^{z/z}$ embryos develop NTDs confirms that integrity of the mitochondrial 1C pathway is essential for normal neural tube development. As illustrated in FIG. 1, mitochondria possess multiple enzymes that produce CH$_2$-THF from various 1C donors (reactions 4m, 5, 8, and 9) (Tibbetts AS & Appling DR (2010) Annu Rev. Nutr. 30:57-81). Embryonic mitochondria also possess redundant dehydrogenase/cyclohydrolase enzymes that can oxidize CH$_2$-THF to 10-CHO-THF (MTHFD2 and MTHFD2L; reactions 2 m and 3 m). MTHFD2 is expressed in transformed cells and embryonic or nondifferentiated tissues, but not in adult differentiated tissues (Christensen KE & Mackenzie RE (2008) Vitam. Horm. 79:393-410). Homozygous knockout of Mthfd2 is embryonic lethal, but does not cause NTDs (Di Pietro E, et al (2002) Mol Cell Biol 22:4158-4166). Mthfd2 nullizygous embryos develop to about E15.5 and display no gross developmental abnormalities, but they are noticeably smaller and paler than wild-type and heterozygous littermates. The lack of NTDs in Mthfd2 nullizygous embryos is likely due to the existence of MTHFD2L, a second mitochondrial dehydrogenase/cyclohydrolase. MTHFD2L is expressed in embryos and adults (Bolusani S, et al. (2011) J. Biol. Chem. 286:5166-5174) and can presumably support mitochondrial 1C flux to the level of 10-formyl-THF in Mthfd2 nullizygous embryos.

On the other hand, only one enzyme with 10-formyl-THF synthetase activity (MTHFD1L) is known to exist in mitochondria, and this activity is required to produce formate and THF from 10-CHO-THF (FIG. 1, reaction 1 m). Thus, loss of MTHFD1L activity is expected to completely abolish mitochondrial formate production. This metabolic block would then starve the cytoplasm for formate, creating a "formyl trap", analogous to the methyl trap seen when 5-methyl-THF accumulates in vitamin $B_{12}$-deficient cells (Herbert V & Zalusky R (1962) J. Clin. Invest. 41:1263-1276; Noronha JM & Silverman M (1962) Vitamin B12 and Intrinsic Factor, 2nd European Symposium, ed Heinrich HC (Verlag, Stuttgart), pp 728-736). Although the Mthfd1l knockout mouse is replete of folate, it has no way to catalyze the conversion of 10-formyl-THF to THF plus formate, leading to a trapping of mitochondrial 1C units as 10-formyl-THF, which cannot exit the mitochondrion. This in turn would cause a deficiency in cytoplasmic 1C units, which are needed in stoichiometric amounts for purine and thymidylate production as well as the methyl cycle. The phenotypes of the Shmt1 and Amt knockout mice are consistent with this model of mammalian 1C metabolism. The Shmt1 gene, which encodes cytoplasmic serine hydroxymethyltransferase (FIG. 1, cytoplasmic reaction 4), is not essential in mice (Macfarlane AJ, et al. (2008) J. Biol. Chem. 283:25846-25853), indicating that mitochondrial SHMT (mitochondrial reaction 4 m) is fully capable of providing all the 1C units needed in both the embryo and the adult. The neural tube phenotype in Amt nullizygous embryos lacking GCS activity (mitochondrial reaction 5) (Narisawa A, et al. (2012) Hum Mol Gen 21:1496-1503) is less severe than that in Mthfd1l knockout embryos. Presumably, the existence of alternative mitochondrial 1C donors (e.g. serine) allows some of the $Amt^{-/-}$ embryos to develop normally. On the other hand, all mitochondrial 1C units, whatever their source, must pass through the MTHFD1L reaction to supply the cytoplasm with formate, and any defect in this step would be expected to cause a more severe phenotype. The importance of mitochondrially-derived formate is demonstrated by the disclosed results showing a significant reduction in the incidence of NTDs and partial rescue of $Mthfd1l^{z/z}$ embryonic growth with maternal formate supplementation.

MTHFD1L thus controls the flux of 1C units from mitochondria into cytoplasmic processes such as purine and thymidylate biosynthesis and the methyl cycle (FIG. 1). De novo purine biosynthesis is essential for cell division, and S-adenosylmethionine (AdoMet) synthesis is critical for chromatin and DNA methylation, which play essential roles during cell differentiation (Bai S, et al. (2005) Mol Cell Biol 25:751-766; Kobayakawa S, et al. (2007) Genes Cells 12:447-460) and cell migration (Horswill MA, et al. (2008) Exp. Eye Res. 86:586-600). Epigenetic modifications are particularly dynamic, with extensive reprogramming of DNA methylation during early embryogenesis (Borgel J, et al. (2010) Nat. Genet. 42:1093-1100). Disruption of the methyl cycle is known to induce NTDs in cultured mouse embryos (Dunlevy L P, et al. (2006) Birth Defects Res A Clin Mol Teratol 76:544-552) and cranial defects are observed in DNA methyltransferase 3b nullizygous embryos (Okano M, et al. (1999) Cell 99:247-257). Recent studies in humans have linked maternal folate status and occurrence of NTDs to tissue-specific DNA hypo- and hypermethylation patterns, with decreased DNA methylation observed in NTD brain tissue compared to normal embryos (Chang H, et al. (2011) J Nutr Biochem 22:1172-1177). Protein methylation is also involved in neural tube development, and hypomethylation of neural tube proteins is accompanied by a failure of the neural tube to close in rat embryos cultured in methionine-deficient conditions (Coelho CN & Klein NW (1990) Teratology 42:437-451). The cytoskeletal proteins β-actin and tubulin are known to be methylated during neural tube closure (Moephuli SR, et al. (1997) Proc. Natl. Acad. Sci. U.S.A. 94:543-548), and proper function of the cytoskeleton is required for cranial neural tube closure (Copp AJ, et al. (2003) Nat Rev Genet 4:784-793).

A common polymorphism in Mthfd1l has been shown to be strongly associated with NTD risk in an Irish population (Parle-McDermott A, et al. (2009) Hum. Mutat. 30:1650-1656), suggesting that MTHFD1L also plays an important role in human neural tube development. Importantly, disruption of MTHFD1L function does not cause cellular folate deficiency (like a transport defect), rather it blocks a specific metabolic step the production and release of formate from mitochondria into the cytoplasm. This metabolic defect causes aberrant neural tube closure including craniorachischisis and exencephaly and/or a wavy neural tube phenotype in 100% of $Mthfd1l^{z/z}$ embryos (FIG. 3).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for reducing the risk of neural tube defects during pregnancy in a subject, comprising administering to a pregnant subject an effective amount of a composition comprising a formate.

2. The method of claim 1, wherein the formate comprises a salt or ester of formic acid.

3. The method of claim 2, wherein the formate comprises calcium formate, sodium formate, ammonium formate, potassium formate, magnesium formate, or a combination thereof.

4. The method of claim 3, wherein the formate comprises calcium formate.

5. The method of claim 1, wherein the composition further comprises vitamin B12.

6. The method of claim 1, wherein the composition further comprises iron.

7. The method of claim 1, wherein the composition further comprises choline.

8. The method of claim 1, wherein the composition comprises about 0.5 mg to about 10,000 mg of the formate.

* * * * *

SEQUENCE LISTING

<160> NUMBER OF SEQ ID NOS: 11

<210> SEQ ID NO 1
<211> LENGTH: 31
<212> TYPE: DNA
<213> ORGANISM: Artificial Sequence
<220> FEATURE:
<223> OTHER INFORMATION: Synthetic Construct

<400> SEQUENCE: 1
gagtatgtga ttgcttggac ccccaggttc c      31

<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

<400> SEQUENCE: 2
tggctcccga ggttgtcttc tggctatgat                                    30

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
cggcgccagc ctgcttttt gtacaaactt g                                   31

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct

<400> SEQUENCE: 4
gcattaccgg tcgatgcaac gagtgatgag                                    30

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
gagtgaacga acctggtcga aatcagtgcg                                    30

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
ttgtctagag agcatggagg gccatgtcaa                                    30

<210> SEQ ID NO 7
<211> LENGTH: 30
<212> TYPE: DNA
<213> ORGANISM: Artificial Sequence
<220> FEATURE:
<223> OTHER INFORMATION: Synthetic Construct

<400> SEQUENCE: 7
ccactcctct gtgacacttt agccctccga                                    30

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ctcacatctg cttgcctcca                                               20

<210> SEQ ID NO 9

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
atgtccccag tcaggtgaag                                              20

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
agagacggcc gcatcttc                                                18

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
caaatggcag ccctggtga                                               19
```